(12) United States Patent
Sakamoto et al.

(10) Patent No.: US 7,746,214 B2
(45) Date of Patent: Jun. 29, 2010

(54) ROTARY VARIABLE RESISTOR

(75) Inventors: Hideyuki Sakamoto, Saitama (JP);
Mitsuyoshi Kanai, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 575 days.

(21) Appl. No.: 11/328,452

(22) Filed: Jan. 10, 2006

(65) Prior Publication Data

US 2006/0176144 A1    Aug. 10, 2006

(30) Foreign Application Priority Data

Feb. 9, 2005    (JP)    ............................. 2005-032586

(51) Int. Cl.
*H01C 10/32* (2006.01)
(52) U.S. Cl. ...................... 338/162; 338/163
(58) Field of Classification Search ................. 338/162
See application file for complete search history.

(56) References Cited

U.S. PATENT DOCUMENTS

| | | | | |
|---|---|---|---|---|
| 3,471,820 A | * | 10/1969 | Young, Jr. | .................... 338/163 |
| 4,295,119 A | | 10/1981 | Kasashima et al. | |
| 4,310,824 A | | 1/1982 | Steigerwald | |
| 4,719,324 A | | 1/1988 | Kuratani | |
| 4,730,506 A | | 3/1988 | Kageyama | |
| 5,469,125 A | * | 11/1995 | Shigemoto et al. | .......... 338/162 |
| 6,005,473 A | | 12/1999 | Ishihara | |
| 6,275,140 B1 | | 8/2001 | Asano | |

FOREIGN PATENT DOCUMENTS

| | | | |
|---|---|---|---|
| CN | 1106158 A | | 8/1995 |
| JP | 6112014 A | | 4/1994 |
| JP | 10-270218 | | 10/1998 |
| JP | 11195509 A | * | 7/1999 |
| JP | 2000260604 A | | 9/2000 |
| JP | 2003-337628 | | 11/2003 |
| TW | 417825 Y | | 1/2001 |
| TW | 511101 B | | 11/2002 |
| TW | 564996 | | 12/2003 |
| TW | 569245 B | | 1/2004 |
| TW | 575883 B | | 2/2004 |

* cited by examiner

*Primary Examiner*—Elvin G Enad
*Assistant Examiner*—Joselito Baisa
(74) *Attorney, Agent, or Firm*—Arent Fox LLP

(57) ABSTRACT

A rotary variable resistor includes a variable resistor body mounted to a console panel, a rotor shaft protruding outward from the variable resistor body, and a control knob coupled to an outer end of the rotor shaft. A single plate-shaped stopper is projectingly provided, along a rotational direction of the rotor shaft, on a front face of the variable resistor body from which the rotor shaft protrudes. First and second restricting portions are provided on the control knob side-by-side along the rotational direction of the rotor shaft to alternately abut against the stopper in defining an actual rotational angle of the rotor shaft.

7 Claims, 6 Drawing Sheets

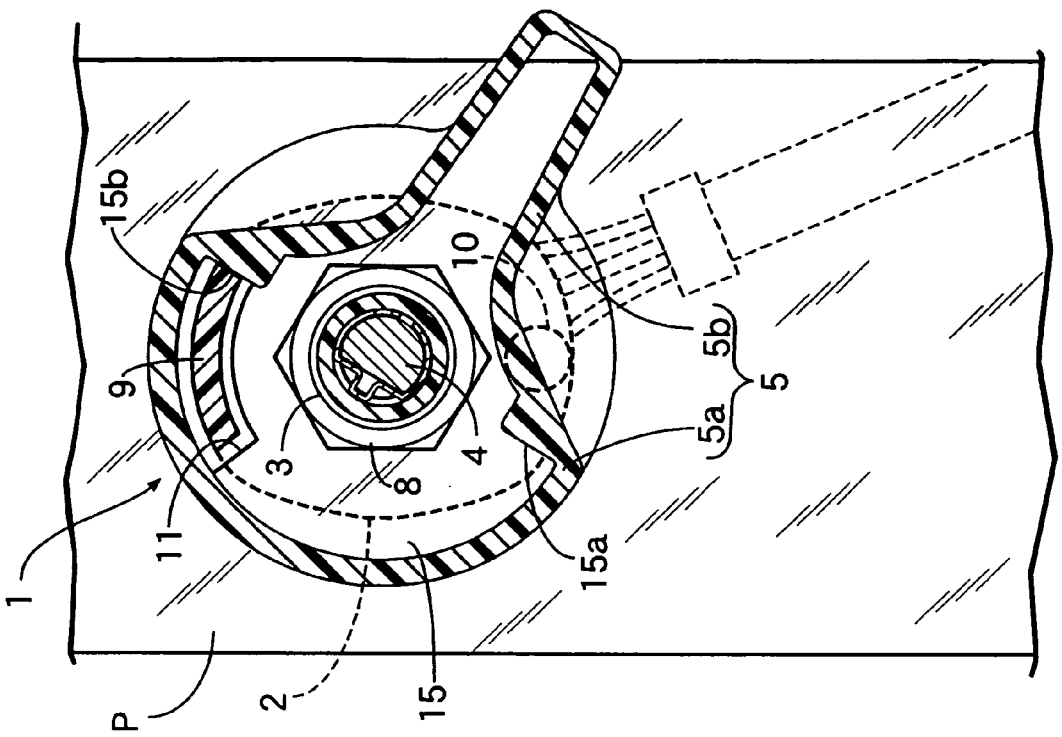
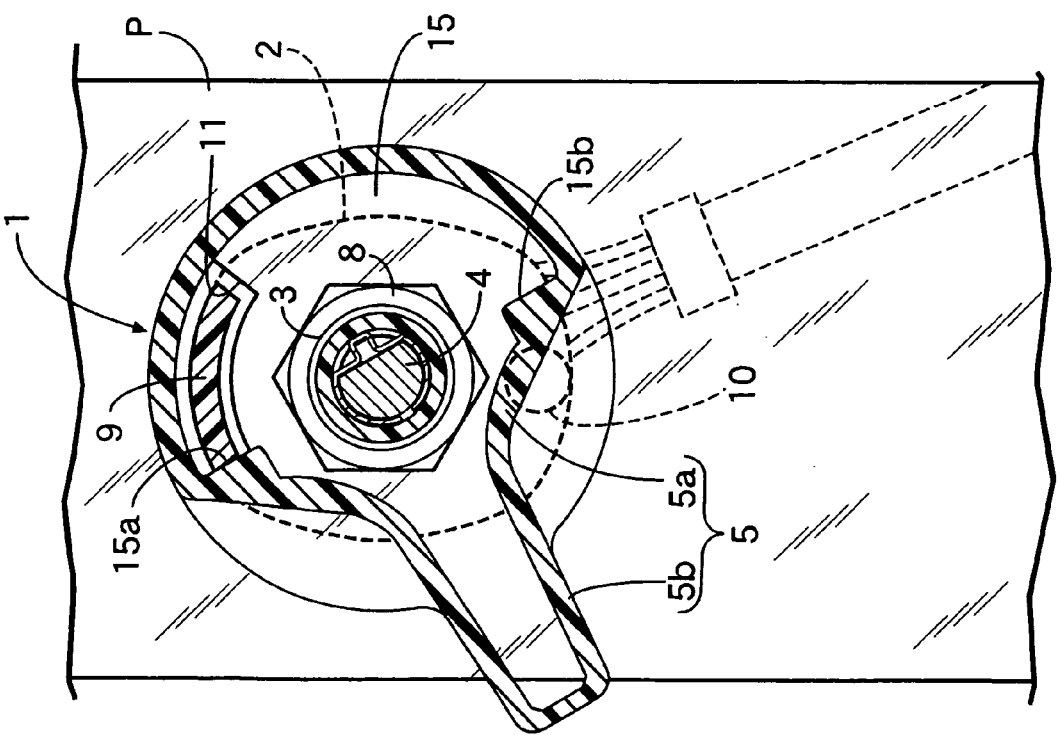

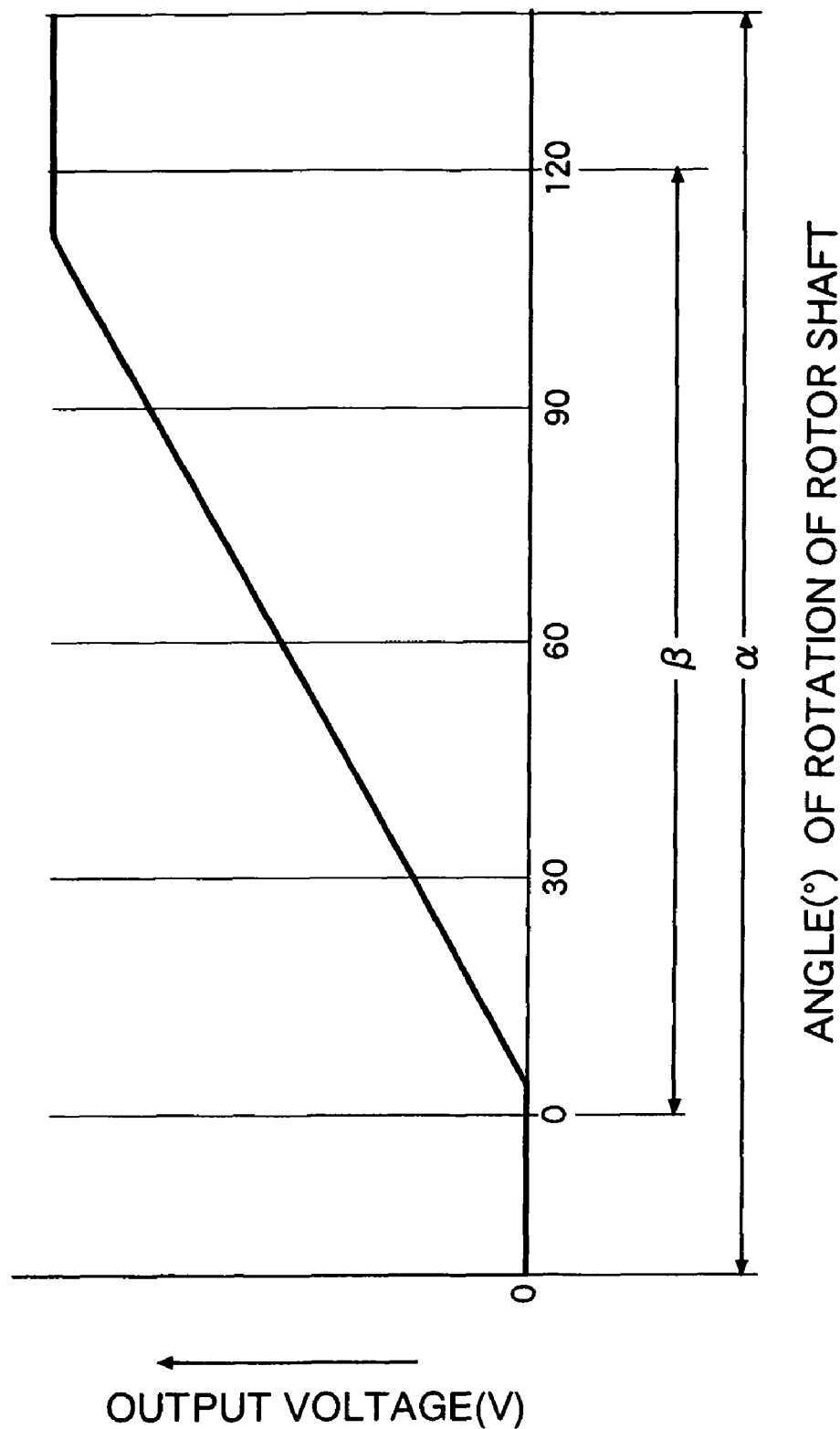

ROTARY VARIABLE RESISTOR

RELATED APPLICATION DATA

The present invention is based upon Japanese priority application No. 2005-32586, which is hereby incorporated in its entirety herein by reference.

BACKGROUND OF THE INVENTION

1. Field of the Invention

The present invention relates to a rotary variable resistor having a variable resistor body mounted to a support member, a rotor shaft rotatably supported on the variable resistor body and protruding outward, and a control knob coupled to an outer end of the rotor shaft.

2. Description of the Related Art

A rotary variable resistor is disclosed in, for example, Japanese Patent Application Laid-open No. 10-270218. In the disclosed rotary variable resistor, a single stopper is provided on a control knob, and a pair of restricting portions are provided on a variable resistor body and alternately receive the stopper to define a rotational angle of a rotor shaft. In some cases, the actual rotational angle of the rotor shaft is changed depending on the application of the variable resistor. However, in the above-identified rotary variable resistor wherein the pair of restricting portions are provided on the variable resistor body and alternately receive the stopper to define the actual rotational angle of the rotor shaft, a plurality of variable resistor bodies having different distances between the pair of restricting portions in correspondence to the required rotational angles of the rotor shaft must be prepared in advance which makes it rather difficult to reduce the cost.

SUMMARY OF THE INVENTION

The present invention has been accomplished with such circumstance in view, and it is an aspect of the present invention to provide a rotary variable resistor, wherein a variable resistor body is universally usable within various variable resistors having rotor shafts with different actual rotational angles to reduce cost.

To achieve the above aspect, according to a first feature of the present invention, there is provided a rotary variable resistor including a variable resistor body mounted to a support member. A rotor shaft is rotatably supported on the variable resistor body and protrudes away therefrom in an outward direction. A control knob is coupled to an outer end of the rotor shaft. A single plate-shaped stopper is projectingly provided along a rotational direction of the rotor shaft and on a front face of the variable resistor body from which the rotor shaft protrudes. First and second restricting portions are provided on the control knob adjacent to each other along the rotational direction of the rotor shaft. The restricting portions alternately abut against the stopper in defining an actual rotational angle of the rotor shaft.

The support member corresponds to a console panel P in an embodiment of the present invention which will be described hereinafter.

According to a second feature of the present invention, in addition to the first feature, a connecting boss fitted around the rotor shaft and an arcuate recess formed radially adjacent to the connecting boss to receive the stopper are formed on an inner end face of the control knob which is opposite the variable resistor body. The arcuate recess has opposite inner end walls which form the first and second restricting portions. The control knob has a tab with a base end that is integrally connected to the first and second restricting portions.

According to a third feature of the present invention, in addition to the first or second feature, the stopper is disposed to serve as a visor covering the rotor shaft from above. A connecting boss fitted around the rotor shaft and an arcuate recess formed radially adjacent to the connecting boss to receive the stopper are formed on an inner end face of the control knob which is opposite the variable resistor body. A labyrinth is defined by an inner peripheral wall of the arcuate recess and the stopper.

With the first feature of the present invention, only one stopper is projectingly provided on the variable resistor body. Therefore, molding of the variable resistor body is possible, and the variable resistor body can be universally used within various types of rotary variable resistors having rotor shafts with different actual rotational angles. Accordingly, a higher degree of productivity results which greatly contributes to the reduction in overall cost per unit. Further, because the stopper has a plate shape extending along the rotational direction of the rotor shaft, the stopper has a high rigidity in the direction of abutment against the first and second restricting portions. Therefore, the stopper is able to withstand the abutment load from the first and second restricting portions, leading to an increase in durability. Because the first and second restricting portions are formed on the control knob, which has a relatively simple structure and shape, advance preparation of different types of control knobs, having different distances between the first and second restricting portions in correspondence to various types of rotary variable resistors having different actual rotational angles of rotor shafts, is relatively easy to accomplish. The increase in cost of resistors having such a structural arrangement is relatively small.

With the second feature of the present invention, the first and second restricting portions have a high rigidity. The restricting portions are defined by the opposing end walls of the arcuate recess formed on the inner end face of the control knob. Further, the base end of the tab is connected to and reinforces the restricting portions to further enhance the rigidity of each restricting portion. Thus, the restricting portions are able to withstand the abutment load from the stopper, therein improving durability.

With the third feature of the present invention, the plate-shaped stopper serves as a visor covering the rotor shaft from above, and the labyrinth is defined by the stopper and the inner peripheral wall of the recess in the control knob for receiving the stopper. Therefore, even when droplets of water, such as rainwater, fall onto the rotary variable resistor, the water droplets are prevented from entering a region around the rotor shaft.

BRIEF DESCRIPTION OF THE DRAWINGS

The present invention will be explained below based on an embodiment of the invention illustrated in the appended drawings.

FIGS. 5A and 5B explain operation of the rotary variable resistor; and

FIG. 6 is a graph showing the output voltage characteristic of the rotary variable resistor.

DETAILED DESCRIPTION OF THE PREFERRED EMBODIMENT

Figure 1:
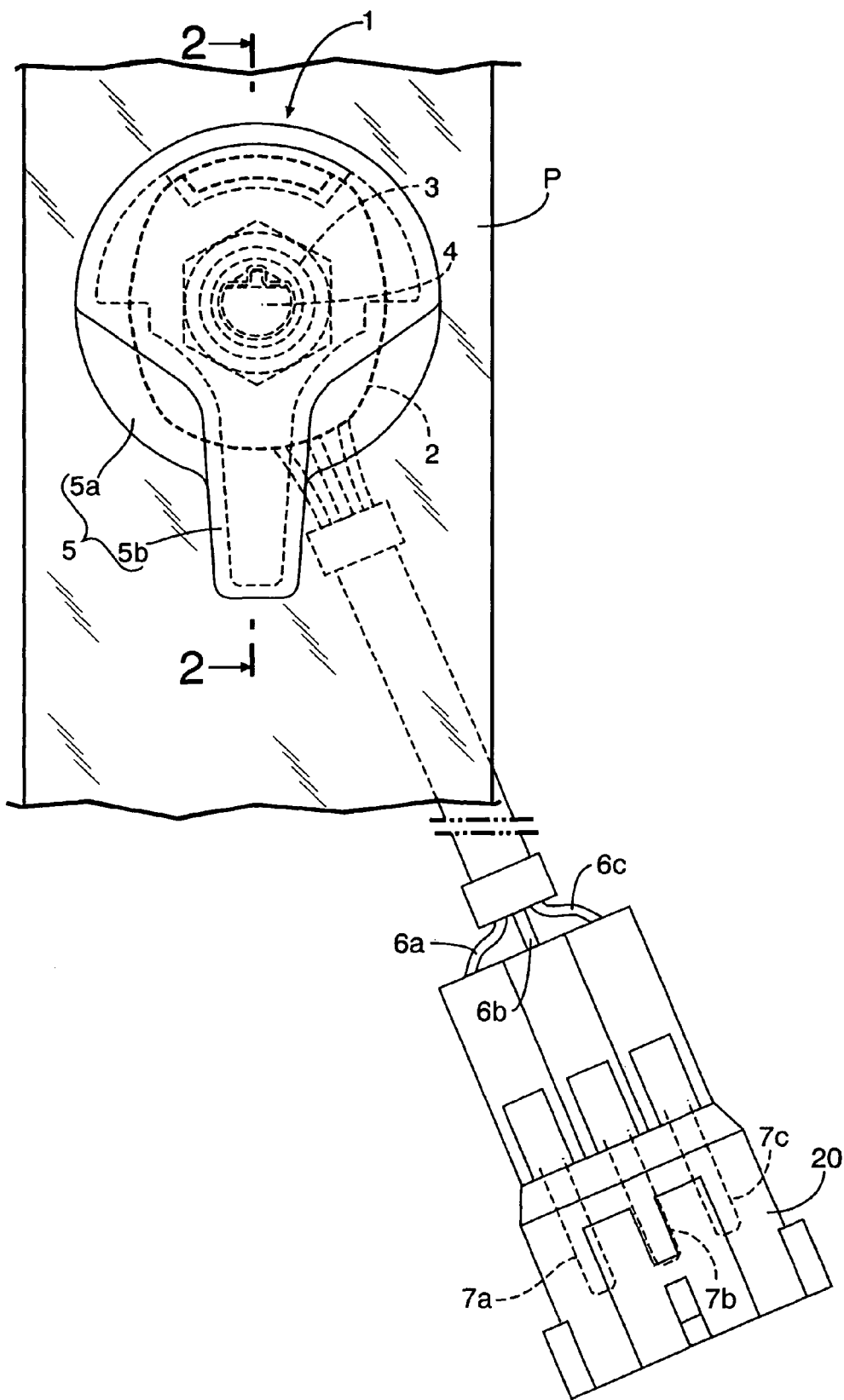
FIG. 1 is a front view of a rotary variable resistor according to a preferred embodiment of the present invention in a state wherein the resistor is mounted to a console panel.
Figure 2:
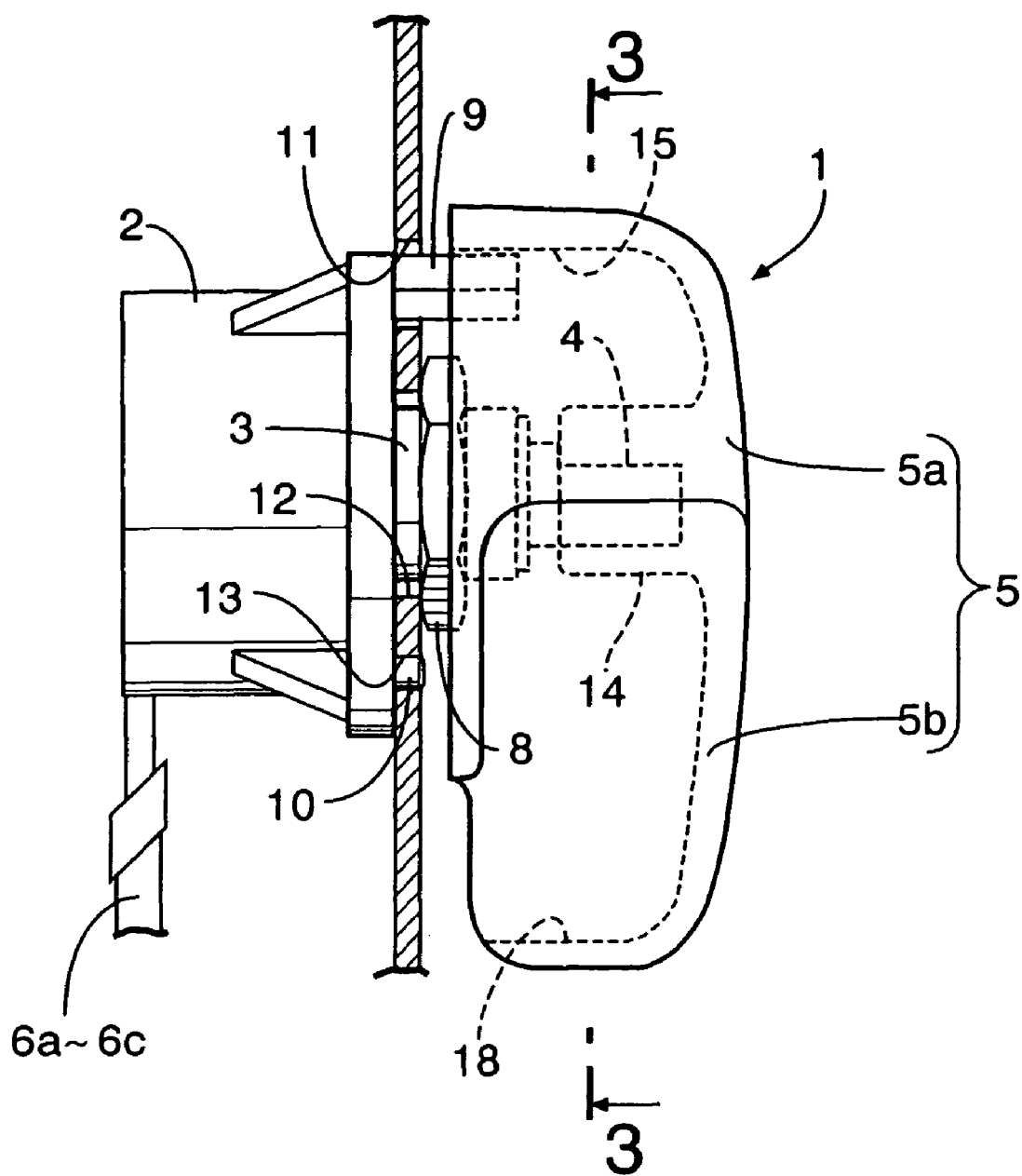
FIG. 2 is a sectional view taken along line 2-2 in FIG. 1.

Referring to FIGS. 1 and 2, a rotary variable resistor 1, according to the present invention, includes a rotary variable resistor body 2 made of a synthetic resin and having a metal bearing tube 3 fixedly mounted on a front end wall thereof; a rotor shaft 4 rotatably supported on the bearing tube 3 and protruding from the front face of the variable resistor body 2; and a control knob 5 made of a synthetic resin and coupled to an outer end of the rotor shaft 4. A resistor substrate is fixed within the variable resistor body 2, and a rotor operable in cooperation with the substrate is accommodated in the variable resistor body 2 (both are not shown). The rotor shaft 4 extends from the rotor.

Figure 3:
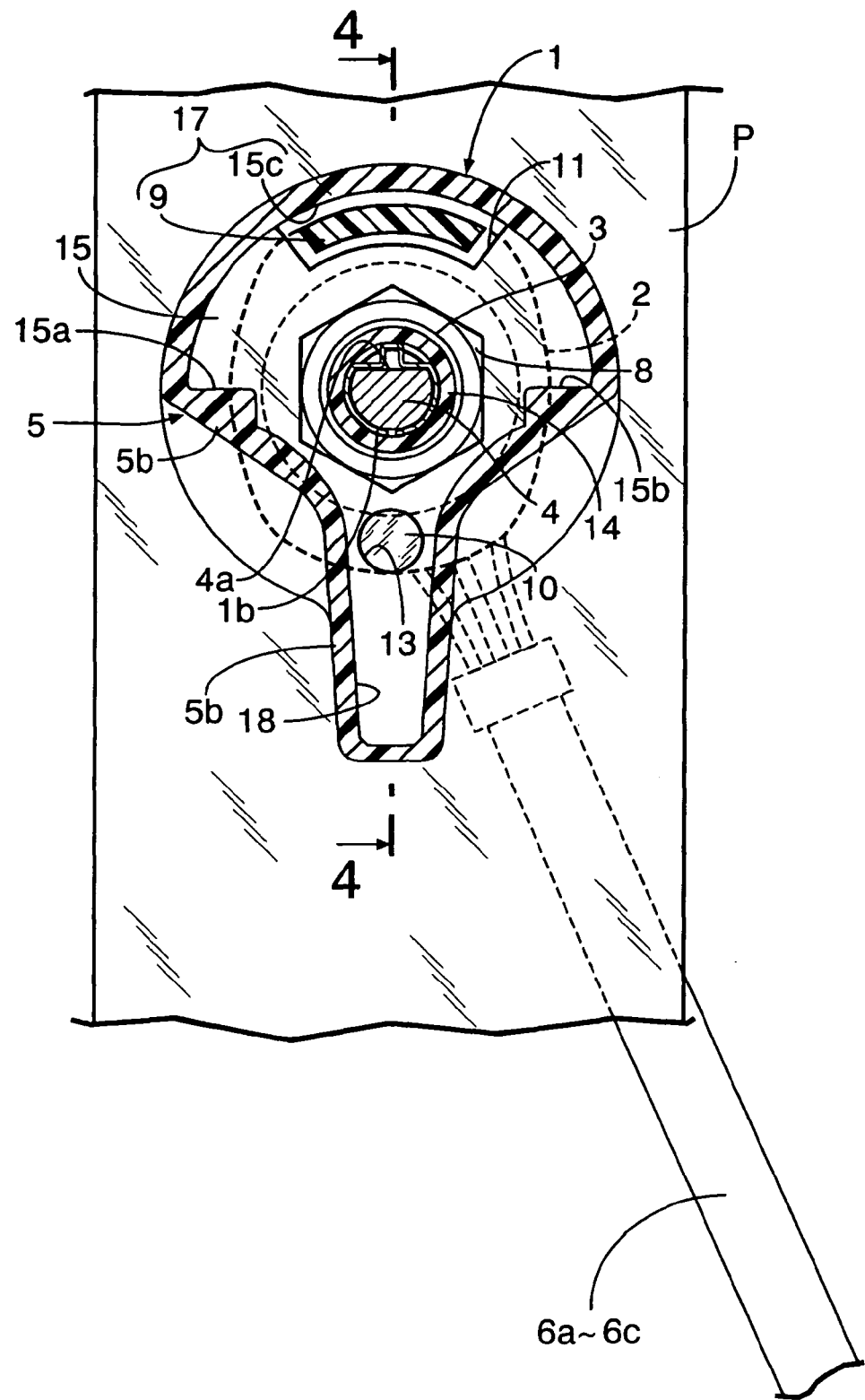
FIG. 3 is a sectional view taken along line 3-3 in FIG. 2.
Figure 4:
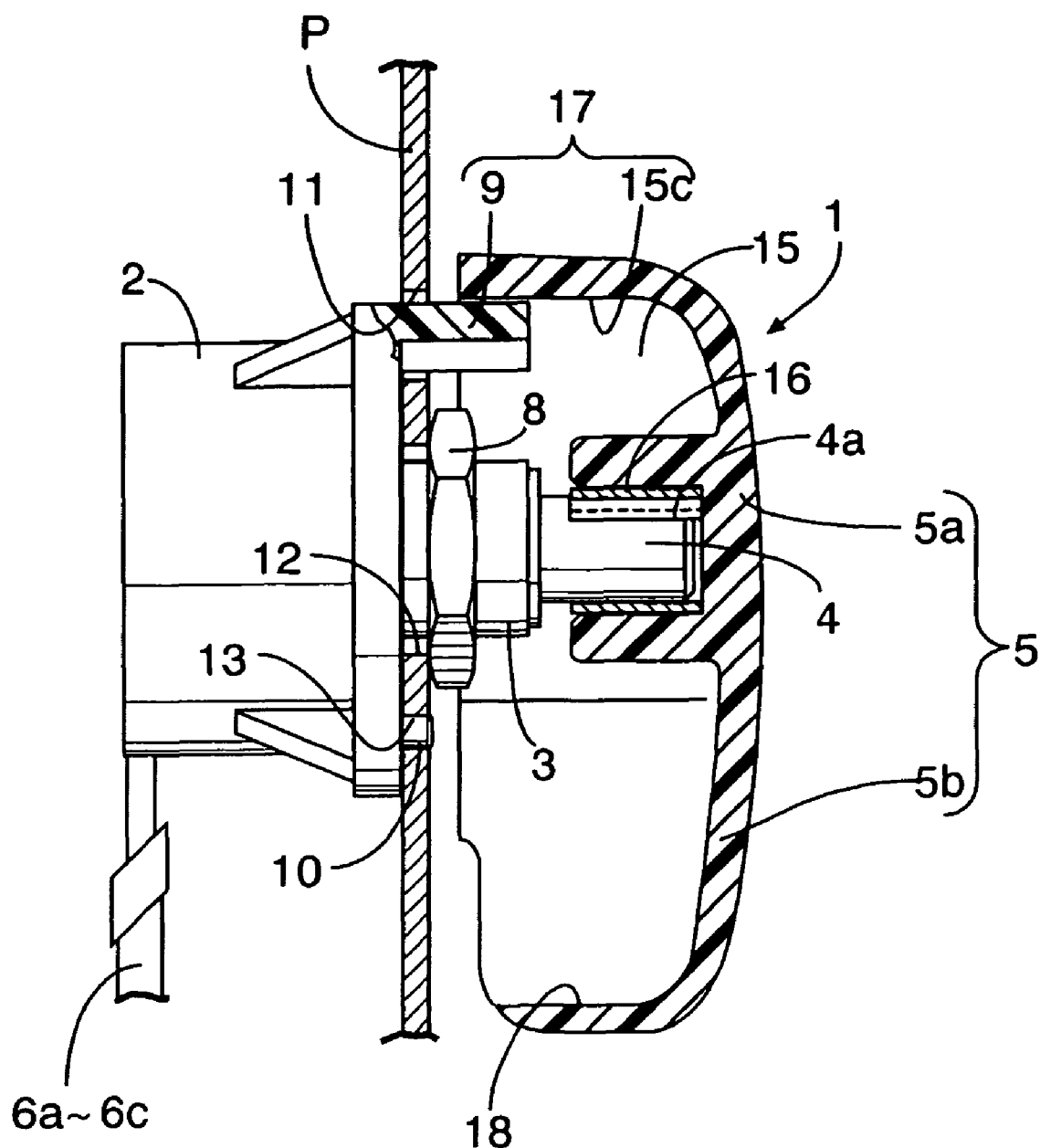
FIG. 4 is a sectional view taken along line 4-4 in FIG. 3.

As shown in FIGS. 1 and 3, lead wires 6a to 6c extend from the variable resistor body 2 toward the resistor substrate. A coupler 20 is connected to the lead wires 6a to 6c and includes connection terminals 7a to 7c leading to the lead wires 6a to 6c. Two of the connection terminals, 7a and 7b, are connected to opposite poles of a standard battery so that a voltage corresponding to an actual rotational angle of the rotor shaft 4 is taken from the plus-pole side terminal 7b and the remaining terminal 7c.

As shown in FIGS. 1 to 4, integrally and projectingly provided on the front face of the variable resistor body 2 is a single stopper 9 having an arcuate plate shape and extending along the rotational direction of the rotor shaft 4 on the side of an outer periphery of the variable resistor body 2. A positioning projection 10 is disposed on a side opposite from the stopper 9 with the rotor shaft 4 therebetween. On the other hand, the console panel P, supporting the variable resistor body 2, is provided with through-holes 11 and 12, through which the stopper 9 and the bearing tube 3 are passed, and a positioning hole 13 into which the positioning projection 10 is fitted. The console panel P is disposed in a substantially upright state.

Thus, to mount the variable resistor body 2 to the console panel P, the stopper 9, the bearing tube 3 and the positioning projection 10 of the rotary variable resistor 1 are inserted through the through-holes 11 and 12 and the positioning hole 13 from the rear side of the console panel P. The front face of the variable resistor body 2 is superposed on the rear face of the console panel P. A nut 8 is threadedly fitted over the bearing tube 3 protruding from the front face of the console panel P. In a state in which the variable resistor body 2 is mounted to the console panel P and tightened, the stopper 9 occupies a position in which the stopper 9 serves as a visor covering the rotor shaft 4 and the bearing tube 3 from above.

A rotation-preventing flat face 4a is formed on one side of an outer end of the rotor shaft 4 protruding outward from the bearing tube 3. The synthetic resin control knob 5 is coupled to the outer end of the rotor shaft 4 and includes a circular knob body 5a and a flat tab 5b protruding to one side from the knob body 5a. Provided on an inner end face of the knob body 5a, opposite the variable resistor body 2, are a connecting boss 14 located at a central portion of the inner end face, and an arcuate recess 15 radially adjacent to and concentric with the connecting boss 14. A retaining spring 16, having a shape conforming to the profile of the outer end of the rotor shaft 4, is mounted to an inner peripheral face of the connecting boss 14. When the outer end of the rotor shaft 4 is fitted inside the retaining spring 16, the connecting boss 14 is connected to the rotor shaft 4 due to a contraction force of the retaining spring 16.

When the control knob 5 is coupled to the rotor shaft 4 in this manner, the arcuate recess 15 of the knob body 5a receives the arcuate stopper 9 of the variable resistor body 2. Moreover, an inner peripheral wall 15c of the recess 15 is located near an outer peripheral face of the stopper 9 to define a labyrinth 17 therebetween.

An inner end wall 15a of the recess 15 forms a first restricting portion for receiving one end face of the stopper 9 to define one of rotational limits of the rotor shaft 4. The other inner end wall 15b of the recess 15 forms a second restricting portion for receiving the other end face of the stopper 9 to define the other rotational limit of the rotor shaft 4. Moreover, the tab 5b, which has a leading end protruding downward, is integrally connected at a base end to the first and second restricting portions 15a and 15b, thereby reinforcing the restricting portions 15a and 15b.

Further, a draining groove 18 is formed in an inner end face of the control knob 5 to extend from the recess 15 to the leading end of the tab 5b.

FIG. 6 shows an output voltage characteristic of the rotary variable resistor 1, wherein α is a maximum rotational angle of the rotor shaft 4 defined within the variable resistor body 2, and β is an actual rotational angle of the rotor shaft 4 defined by the abutment of the first and second restricting portions 15a and 15b against the stopper 9. Therefore, if the positions of the first and second restricting portions 15a and 15b and the distance therebetween are changed, the rotational angle β and the position of the rotor shaft 4 are changeable.

The operation of the above-described embodiment will be described below.

If the tab 5b of the control knob 5 is pinched and rotated in a clockwise direction, as shown in FIG. 5A, the voltage taken out of the connection terminals 7b and 7c of the coupler 20 is lowered (or raised) and reaches a lowest (or highest) level upon abutment of the first restricting portion 15a of the control knob 5 against the stopper 9 of the variable resistor body 2. On the other hand, if the control knob 5 is rotated in a counterclockwise direction, as shown in FIG. 5B, the voltage taken out of the connection terminals 7b and 7c of the coupler 20 is raised (or lowered) and reaches a highest (or lowest) level upon abutment of the second restricting portion 15b of the control knob 5 against the stopper 9 of the variable resistor body 2.

Because only one stopper 9 is projectingly provided on the front face of the variable resistor body 1, molding of the variable resistor body 2 is possible, and the variable resistor body 2 is universally usable with various types of rotary variable resistors 1 having rotor shafts with different actual rotational angles, leading to a higher degree of productivity and greatly reduced cost. Further, because the stopper 9 has a plate shape extending along the rotational direction of the rotor shaft 4, the stopper 9 has a high rigidity in the direction of abutment against the first and second restricting portions 15a and 15b. Therefore, the stopper 9 sufficiently withstands the abutment loads from the first and second restricting portions 15a and 15b, resulting in increased durability.

The first and second restricting portions 15a and 15b are formed by opposite end walls of the arcuate recess 15 formed in the inner end face of the control knob 5, and each has a relatively high rigidity. Further, because the base end of the tab 5b is connected to and reinforces the restricting portions 15a and 15b, the restricting portions 15a and 15b have an enhanced rigidity. Therefore, the restricting portions 15a and 15b are able to withstand the abutment load from the stopper 9, leading to improved durability. Furthermore, because the control knob 5 has a relatively simple structure and shape, and is easy to mold, it is relatively easy to prepare, in advance, a plurality of different types of control knobs 5 with different distances between the first and second restricting portions 15a and 15b in correspondence to various types of rotary variable resistors having different actual rotational angles of rotor shafts. Any increase in cost to produce such resistors is relatively small. Eventually, the cost can be reduced in the entirety of the rotary variable resistor 1.

The arcuate plate-shaped stopper 9 serves as the visor covering the rotor shaft 4 and the bearing tube 3 supporting the rotor shaft 4 from above, and the labyrinth 17 is defined by the stopper 9 and the inner peripheral wall 15c of the recess 15 of the control knob 5 which accommodates the stopper 9. Therefore, when droplets of water, such as rainwater, fall onto the rotary variable resistor 1, it is possible to prevent the water droplets from entering a portion around the bearing tube 3, i.e., around the rotor shaft 4. Even if the water droplets entered the labyrinth 17, the water droplets would drip downward in the recess 15 from the opposite end edges of the stopper 9 without falling onto the bearing tubes 3 and the rotor shaft 4, and would flow outward through the draining groove 18 in the rear face of the tab 5b.

It should be noted that although a preferred embodiment of the present invention has herein been described, various modifications in the present invention may be made without departing from the scope, spirit and subject matter thereof.

The invention claimed is:

1. A rotary variable resistor comprising:
   a support member;
   a variable resistor body having a front face mounted directly to a rear face of the support member;
   a bearing tube extending through a first aperture defined in the support member and away from a front face of the support member;
   a rotor shaft rotatably supported on the bearing tube and protruding away from the front face of the variable resistor body;
   a control knob coupled to an outer end of the rotor shaft, wherein the support member is disposed entirely between the variable resistor body and the control knob;
   a plate-shaped stopper extending through a second aperture defined in the support member and projectingly provided, along a rotational direction of the rotor shaft, on the front face of the variable resistor body from which the rotor shaft protrudes; and
   first and second restricting portions provided on the control knob in a side-by-side arrangement relative to each other and along the rotational direction of the rotor shaft,
   wherein the first and second restricting portions alternately abut against the stopper and define an actual rotational angle ($\beta$) of the rotor shaft.

2. The rotary variable resistor according to claim 1, further comprising a connecting boss fitted around the rotor shaft and an arcuate recess formed radially adjacent to the connecting boss to receive the stopper, wherein the connecting boss and arcuate recess are formed on an inner end face of the control knob which opposes the variable resistor body, wherein the arcuate recess has opposite inner end walls which define the first and second restricting portions, and wherein the control knob includes a tab having a base end integrally connected to the first and second restricting portions.

3. The rotary variable resistor according to claim 1, wherein the stopper covers the rotor shaft from above;
   the rotary variable resistor further comprising a connecting boss fitted around the rotor shaft and an arcuate recess formed radially adjacent to the connecting boss to receive the stopper, wherein the connecting boss and arcuate recess are formed on an inner end face of the control knob which opposes the variable resistor body; and a labyrinth formed by an inner peripheral wall of the arcuate recess and the stopper.

4. The rotary variable resistor according to claim 2, wherein the stopper covers the rotor shaft from above.

5. The rotary variable resistor according to claim 2, further comprising a labyrinth formed by an inner peripheral wall of the arcuate recess and the stopper.

6. The rotary variable resistor according to claim 1, wherein the support member is plate shaped.

7. The rotary variable resistor according to claim 1, wherein the rotor shaft extends completely through the support member.

* * * * *